US012734199B2

(12) United States Patent
Duan et al.

(10) Patent No.: US 12,734,199 B2
(45) Date of Patent: Sep. 15, 2026

(54) COMBINED FORMULATION CAPABLE OF AMELIORATING GASTROINTESTINAL ADVERSE EFFECTS CAUSED BY OXALIPLATIN AND PREPARATION METHOD THEREFOR AND USE THEREOF

(71) Applicant: NANJING UNIVERSITY OF CHINESE MEDICINE, Nanjing (CN)

(72) Inventors: Jinao Duan, Nanjing (CN); Sheng Guo, Nanjing (CN); Wanchen Cui, Nanjing (CN); Haifeng Liu, Nanjing (CN)

(73) Assignee: NANJING UNIVERSITY OF CHINESE MEDICINE, Nanjing (CN)

( * ) Notice: Subject to any disclaimer, the term of this patent is extended or adjusted under 35 U.S.C. 154(b) by 225 days.

(21) Appl. No.: 18/754,218

(22) Filed: Jun. 26, 2024

(65) Prior Publication Data

US 2024/0342225 A1 Oct. 17, 2024

(30) Foreign Application Priority Data

Dec. 25, 2023 (CN) ........................ 202311799637.7

(51) Int. Cl.

| | |
|---|---|
| ***A61K 39/00*** | (2006.01) |
| ***A61K 31/715*** | (2006.01) |
| ***A61K 35/741*** | (2015.01) |
| ***A61K 36/815*** | (2006.01) |
| ***A61P 1/00*** | (2006.01) |
| ***A61P 1/08*** | (2006.01) |
| ***A61P 1/18*** | (2006.01) |

(52) U.S. Cl.
CPC .......... *A61K 35/741* (2013.01); *A61K 36/815* (2013.01); *A61P 1/00* (2018.01); *A61K 2236/331* (2013.01); *A61K 2236/333* (2013.01); *A61K 2236/51* (2013.01)

(58) Field of Classification Search
CPC ...... A61K 31/01; A61K 31/05; A61K 31/715; A61K 2035/115; A61K 2236/333; A61K 2236/51; A61P 1/00; A61P 1/08
See application file for complete search history.

(56) References Cited

U.S. PATENT DOCUMENTS

2021/0113596 A1* 4/2021 von Maltzahn ........ A61K 31/11

* cited by examiner

*Primary Examiner* — Maryam Monshipouri
(74) *Attorney, Agent, or Firm* — CBM PATENT CONSULTING, LLC

(57) ABSTRACT

Disclosed in the present invention is a combined formulation capable of ameliorating gastrointestinal adverse effects caused by oxaliplatin, which comprises *Lycium barbarum* polysaccharides and *Akkermansia muciniphila*; the *Lycium barbarum* polysaccharide is obtained by removing small molecular substances by ethanol extraction, then continuously performing reflux extraction by using water, and separating by using a hollow fiber ultrafiltration device; *Akkermansia muciniphila* is *Akkermansia muciniphila* ATCC BAA835; the combined formulation provided by the present invention can ameliorate intestinal injury, reduce inflammatory factors and maintain intestinal barriers, and thus can be used as a functional food or a medicine to ameliorate gastrointestinal adverse effects caused by oxaliplatin.

7 Claims, 6 Drawing Sheets

COMBINED FORMULATION CAPABLE OF AMELIORATING GASTROINTESTINAL ADVERSE EFFECTS CAUSED BY OXALIPLATIN AND PREPARATION METHOD THEREFOR AND USE THEREOF

CROSS-REFERENCE TO RELATED APPLICATIONS

This application claims priority to Chinese Patent Application Ser. No. CN2023117996377 filed on 25 Dec. 2023.

TECHNICAL FIELD

The present invention belongs to the field of biopharmaceuticals, and mainly relates to a combined formulation capable of ameliorating gastrointestinal adverse effects caused by oxaliplatin and a preparation method therefor and use thereof. The combined formulation comprises a *Lycium barbarum* polysaccharide and *Akkermansia muciniphila.*

BACKGROUND

Prebiotics are organic substances that are not digested and absorbed by the host but can selectively promote the metabolism and proliferation of beneficial bacteria in the body, thereby improving the health of the host. The commonly used prebiotics include oligosaccharides, microalgaes, polysaccharides, protein hydrolysates, etc. In daily dietary intake, polysaccharides contained in natural vegetables and some medicinal and edible Chinese herbal medicines can be used as prebiotics. *Lycium barbarum* polysaccharide is a natural polysaccharide that has various pharmacological activities. In recent years, it has been reported that *Lycium barbarum* polysaccharide can selectively promote the proliferation of some intestinal beneficial bacteria such as *Lactobacillus acidophilus* and *Bifidobacterium* so as to promote intestinal balance, protect intestinal barrier and promote intestinal health, making *Lycium barbarum* polysaccharide become a potential prebiotic.

Probiotics change the composition of flora at a certain part of a host by colonization in the human body and are a type of active microorganisms that are beneficial to a host. They can promote nutrient absorption and maintain intestinal health by regulating the mucosal and systemic immune functions of the host or regulating the balance of flora in the intestinal tract. *Akkermansia muciniphila* is a mucinolytic bacterium that colonizes the intestinal mucus layer. In recent years, there have been increasing reports about AKK, with much evidence suggesting a negative correlation between AKK and obesity, diabetes, cardiovascular disease and low-grade inflammation; AKK can also play a metabolic protective role by protecting the integrity of intestinal epithelial cells and the mucus layer; AKK supplementation can also relieve enteritis symptoms, regulate immune response in the spleen, intestinal tract and mesenteric lymph node, reduce the inflammation level in the intestinal tract, and prevent intestinal cancer caused by enteritis, and thus is a star product in next-generation probiotics.

Oxaliplatin is a third-generation platinum anti-cancer drug that is mainly used for first- and second-line therapies in advanced colorectal cancer and postoperative adjuvant chemotherapy for patients at an early stage, and is effective on various tumors. However, oxaliplatin, like first- and second-generation platinum anti-cancer drugs, may cause adverse effects and thus seriously affect the life quality of patients. The common adverse effects of oxaliplatin are as follows:

1. Nervous system: acute and dose-accumulative peripheral sensory neuropathy, and duloxetine is currently recommended for the treatment of neuropathy;
2. Blood system: neutropenia, thrombocytopenia, etc., and the recombinant human granulocyte colony stimulating factor is adopted for treatment;
3. Liver and kidney toxicity, and conventional hepatoprotective drugs are adopted; and
4. Gastrointestinal tract: diarrhea, nausea, vomiting, mucositis, loss of appetite, and intestinal barrier impairment, and spleen-strengthening traditional Chinese medicine and composite probiotic supplement are clinically available, but there is no specific directional probiotic supplement.

SUMMARY

The present invention provides a combined formulation of a *Lycium barbarum* polysaccharide and *Akkermansia muciniphila* and use thereof in the amelioration of gastrointestinal adverse effects caused by oxaliplatin. The polysaccharide is prepared from *Fructus lycii*, and the *Akkermansia muciniphila* is purchased from ATCC, with a strain number of ATCC BAA835. Animal experiments show that the formulation can improve intestinal health by reducing the levels of inflammatory factors such as serum TNF-α and IL-6, maintaining the intestinal barrier, reducing the content of serum LPS and reducing intestinal mucosa impairment, thereby significantly ameliorating gastrointestinal adverse effects caused by oxaliplatin. The gastrointestinal adverse effects include, but are not limited to: decreased food intake, weight loss, intestinal barrier impairment, and intestinal mucosa impairment.

Provided is a combined formulation capable of ameliorating gastrointestinal adverse effects caused by oxaliplatin, which comprises a *Lycium barbarum* polysaccharide and *Akkermansia muciniphila.*

The *Akkermansia muciniphila* is in the form of a bacterial powder when in use, and the *Lycium barbarum* polysaccharide is in the form of a powder when in use. The composition in the application is lyophilized powder.

As a preferred embodiment, in the combined formulation for ameliorating gastrointestinal adverse effects caused by oxaliplatin, the *Lycium barbarum* polysaccharide comprises one of *Lycium barbarum* polysaccharides with molecular weights of $2.28\times10^5$ Da, $9.19\times10^4$ Da, $3.03\times10^4$ Da and 1800 Da and an unpurified *Lycium barbarum* polysaccharide;

the *Akkermansia muciniphila* is purchased from the American Type Culture Collection (ATCC), with a strain number of ATCC BAA-835, and is stored in the Jiangsu Collaborative Innovation Center of Chinese Medicinal Resources Industrialization.

As a preferable embodiment, the combined formulation capable of ameliorating gastrointestinal adverse effects caused by oxaliplatin is in the form of a capsule, and a composition further comprises an edible excipient:

the excipient comprises one or more of a diluent, a lyoprotectant, a suspending agent, a flavoring agent, and a solubilizer.

As a preferable embodiment, in the combined formulation for ameliorating gastrointestinal adverse effects caused by oxaliplatin, the *Lycium barbarum* polysaccharide is a *Lycium barbarum* polysaccharide with a molecular weight of $9.19\times10^4$ Da, and has a content of 22 mg/1 part when in use; the *Akkermansia muciniphila* has a viable count of $1\times10^8$ CFU/1 part when in use.

As a preferable embodiment, in the combined formulation for ameliorating gastrointestinal adverse effects caused by oxaliplatin, the *Lycium barbarum* polysaccharide is prepared by the following method:

(1) taking *Fructus lycii*, adding 80% ethanol at a volume ratio of 1:8-1:20, and continuously performing reflux extraction for 1-3 h to obtain an ethanol extract and residues;

(2) adding water into the ethanol extract residues obtained in the step (1) at a ratio of 1:8-1:10, and continuously performing reflux extraction for 1-3 h to obtain a water extract;

(3) concentrating the water extract obtained in the step (2), lyophilizing a part of the concentrated solution to obtain an unpurified *Lycium barbarum* polysaccharide, and purifying a part of the concentrated solution by using a hollow fiber ultrafiltration device to obtain a retention solution; and (4) precipitating the retention solution obtained in the step (3) in ethanol, collecting a precipitate, and lyophilizing the precipitate to obtain *Lycium barbarum* polysaccharides with different molecular weights.

As a preferable embodiment, in the combined formulation for ameliorating gastrointestinal adverse effects caused by oxaliplatin, the *Lycium barbarum* polysaccharide is prepared by the following method:

(1) taking *Fructus lycii*, adding 80% ethanol at a volume ratio of 1:10, and continuously performing reflux extraction for 2 times (2 h each time) to obtain an ethanol extract and residues;

(2) adding water into the ethanol extract residues obtained in the step (1) at a ratio of 1:10, and continuously performing reflux extraction for 2 times (2 h each time) to obtain a water extract;

(3) concentrating the water extract obtained in the step (2), lyophilizing a part of the concentrated solution to obtain an unpurified *Lycium barbarum* polysaccharide, and purifying a part of the concentrated solution by using a hollow fiber ultrafiltration device to obtain a retention solution, wherein ultrafiltration membrane retention capacities are 100 KDa, 50 KDa and 3 KDAa in sequence, and ultrafiltration conditions are 0.1 MPa, 27° C. and 1 g/L; and (4) adding ethanol into the retention solution obtained in the step (3) until a content of the ethanol is 75%, standing for 24 h, collecting a precipitate, and lyophilizing the precipitate to obtain *Lycium barbarum* polysaccharides with different molecular weights.

As a preferable embodiment, in the combined formulation for ameliorating gastrointestinal adverse effects caused by oxaliplatin, a bacterial powder of the *Akkermansia muciniphila* is prepared by the following method:

(1) taking out a cryopreserved strain, thawing the cryopreserved strain in a liquid culture medium, and performing subculturing to obtain a bacterial solution;

(2) centrifuging the bacterial solution obtained in the step (1), collecting a precipitate, and washing the precipitate with normal saline to obtain a bacterial sludge; and (3) adding a composite lyoprotectant into the bacterial sludge obtained in the step (2), and lyophilizing the mixture to obtain the bacterial powder.

As a preferred embodiment, in the combined formulation for ameliorating gastrointestinal adverse effects caused by oxaliplatin, the liquid culture medium used in the step (1) is BHI brain-heart leach liquor+0.25% mucin, and an inoculation amount is 5% per passage;

centrifugation conditions of the step (2) are 7500 r/min, 4° C. and 15 min;

a volume ratio of an addition amount of the composite lyoprotectant to the bacterial sludge in the step (3) is 1:1; the composite lyoprotectant is a solution of 12% of sweet whey powder, 0.4% of glycine, 1.2% of mannitol and 0.2% of VC sodium in percentage by mass prepared from normal saline.

The present invention has the following beneficial effects: the combined formulation of the *Lycium barbarum* polysaccharide and the *Akkermansia muciniphila*, which is prepared in the present invention, can promote intestinal health by reducing the levels of inflammatory factors such as serum TNF-α and IL-6, reducing the content of serum lipopolysaccharide (LPS), maintaining the normal form of the intestinal mucosa and maintaining the intestinal barrier, thereby ameliorating the gastrointestinal adverse effects caused by oxaliplatin, including weight loss, loss of appetite, intestinal mucosa injury, and intestinal barrier impairment.

The combined formulation provided by the present invention can be used as a probiotic formulation, including, but not limited to, chemotherapy adjuvant drugs, and functional health products or medicines.

DETAILED DESCRIPTION

Figure 1:
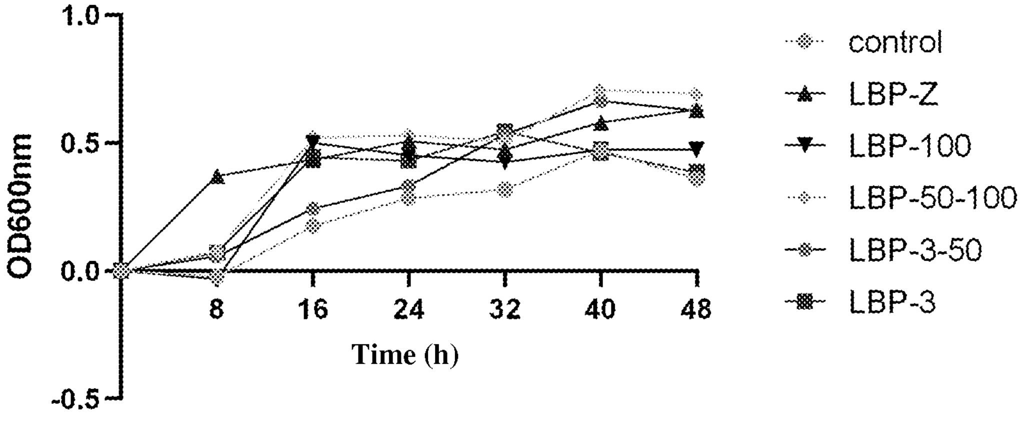
FIG. 1 shows the proliferation effect of five *Lycium barbarum* polysaccharides on *Akkermansia muciniphila;*

The present invention will be described in further detail with reference to specific examples, which are not intended to limit the present invention but only to illustrate the present invention. Unless otherwise stated, the experimental methods used in the following examples, and the experimental methods without specific conditions indicated in the examples are generally performed under conventional conditions. Unless otherwise stated, the materials, reagents and the like used in the following examples are commercially available.

The following descriptions are only preferred examples of the present invention and are not intended to limit the present invention, and various modifications and changes may be made by those skilled in the art. Any modifications, equivalent replacements, improvements, and the like that are made within the spirit and principle of the present invention shall all fall within the protection scope of the present invention.

Example 1: Preparation Method for Combined Formulation of *Lycium barbarum* Polysaccharide and *Akkermansia muciniphila*, Comprising the Following Steps 1.1. Preparation of *Lycium barbarum* polysaccharides:

1.5 kg of *Fructus lycii* was taken, reflux extraction was continuously performed with ten times of 80% ethanol for 2 times (2 h each time), and residues were collected; reflux extraction was continuously performed on the residues for 2 times (2 h each time) by using 10 times of deionized water 100, water extracts were combined, the content of polysaccharides was detected by using a phenol-sulfuric acid method, and the polysaccharides were concentrated under reduced pressure to 1 g/L to obtain an unpurified *Lycium barbarum* polysaccharide;

then the *Lycium barbarum* polysaccharide was treated by adopting a hollow fiber ultrafiltration device (the ultrafiltration membrane retention capacities were 100 KDa, 50 KDa and 3 KDAa in sequence) under the conditions of 0.1 MPa, 27° C. and 1 g/L, ethanol was added into the retention solution, and the concentration was adjusted to 75%. The solution was left to stand for 24 h, and the precipitate was taken out, washed with ethanol, and lyophilized to obtain *Lycium barbarum* polysaccharides LBP-100, LBP-50-100, LBP-3-50 and LBP-3 with different molecular weights.

1.2. Preparation of a Bacterial Powder of *Akkermansia muciniphila:* 0.4 g of BHI Solid culture medium and 25 mg of mucin were weighed, the BHI solid culture medium and the mucin were dissolved in 10 mL of deionized water, the mixture was sterilized at 120° C. for 15 min in a high-temperature high-pressure sterilizer, and the sterilized solution was cooled to room temperature; a cryopreserved strain was taken out, the cryopreserved strain was inoculated in a culture medium by one transfer with a 10-μL inoculating loop, and cultured in an anaerobic incubator at 37° C. for 48 h, then the culture medium was expanded to 1 L after 2 subcultures, and the culture medium was centrifuged at 7500 r/min and 4° C. for 15 min; the bacterial sludge was washed for 3 times with normal saline, and the bacterial sludge was mixed with a composite lyoprotectant (a solution of 12% of sweet whey powder, 0.4% of glycine, 1.2% of mannitol and 0.2% of VC sodium in percentage by mass prepared from normal saline) at a volume ratio of 1:1, and the mixture was lyophilized to obtain the bacterial powder.

Example 2: Screening of Prebiotic Effect of *Lycium barbarum* Polysaccharides This example is directed to screening of the prebiotic activity of two intestinal bacteria with different *Lycium barbarum* polysaccharides.

1.1. Instruments, Reagents and Materials

*Akkermansia muciniphila* (AKK) with the strain number of ATCC BAA-835*; Bifidobacterium bifidum* (BIF) with the strain number of ATCC 15696; BHI brain-heart leach liquor from Guangdong HuanKai Microbial Sci. & Tech. Co., Ltd., 024053; pig gastric mucin from Shanghai Yuan Ye Bio-Technology Co., Ltd., S12066-5g; MRS culture medium from Qingdao Hopebiol, HB0384-5; a microplate reader; an anaerobic workstation.

1.2. Strain Activation

A cryopreserved strain of *Bifidobacterium bifidum* (BIF) was taken and inoculated in 10 mL of a sterilized MRS culture medium; a cryopreserved strain of *Akkermansia muciniphila* (AKK) was taken and inoculated into 10 mL of a sterilized BHI culture medium (containing 0.25% mucin), cultured for 48 h at 37° C. in an anaerobic workstation, and then continuously passaged 2 times to obtain a seed solution.

1.3. Fermentation

As shown in Table 1, 10 mL of a culture medium was prepared, the *Lycium barbarum* polysaccharides with different molecular weights prepared in Example 1 were added to the culture medium to enable the concentration of the *Lycium barbarum* polysaccharides to be 5 mg/mL, and then the culture medium was pasteurised.

The mother liquor was inoculated into each group according to an inoculation amount of 5%, the culture medium was cultured for 48 h at 37° C. in an anaerobic workstation, and the OD value was measured by using a microplate reader at 600 nm every 8 h.

TABLE 1

| Lycium barbarum polysaccharide | Abbreviation | Addition amount of 10 mL BHI culture medium |
|---|---|---|
| Unpurified total polysaccharide | LBP-Z | 50 mg |
| 100 kDa retention solution | LBP-100 | 50 mg |
| 50-100 KDa retention solution | LBP-50-100 | 50 mg |
| 3-50 KDa retention solution | LBP-3-50 | 50 mg |
| 3 kDa effluent | LBP-3 | 50 mg |

As shown in FIG. 1, different *Lycium barbarum* polysaccharides had prebiotic effects on BIF and AKK; the growth cycle was shortened and the maximum OD value was increased, indicating that there were more viable counts. Among them, LBP-50-100 and LBP-Z were preferred, and LBP-50-100 had a stronger prebiotic effect.

Example 3: Measurement of Molecular Weight of LBP-50-100

Figure 2:
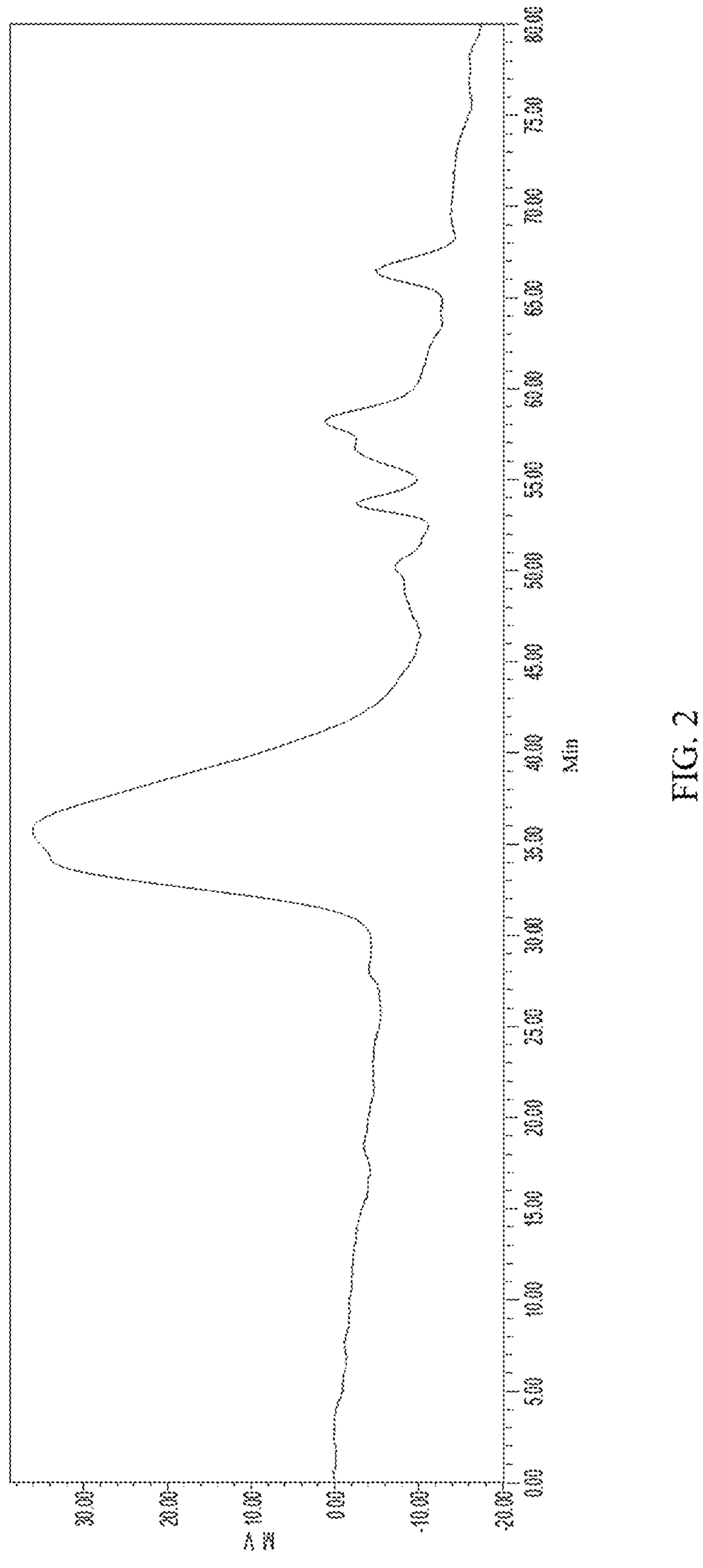
FIG. 2 shows the LBP-50-100 molecular weight measurement results.

2 mg/mL of a PBS buffer of prepared LBP-50-100 was prepared, and the molecular weight was measured by using a high-performance gel permeation chromatography (HPGPC) with a refractive index detector (RID) under the elution conditions of 0.01 M PBS, 0.4 mL/min. A calibration curve was drawn by taking glucan as a standard, and the weight average molecular weight was estimated. The measurement results are shown in FIG. 2, and the molecular weight was calculated to be $9.19\times10^4$ Da.

Example 4: Experiment on Effect of Ameliorating Gastrointestinal Adverse Effects Induced by Oxaliplatin In this example, according to the conclusion obtained in Example 2, the AKK bacterial powder and the *Lycium barbarum* polysaccharides LBP-Z and LBP-50-100 obtained in Example 1 were separately used and combined for use in an in-vivo experiment on a mouse model with gastrointestinal adverse effects induced by oxaliplatin, so as to verify the effect of the combined substance in ameliorating the gastrointestinal adverse effects induced by oxaliplatin.

1. Experimental Method:

(1) The cultured AKK lyophilized bacterial powder was redissolved in sterile normal saline to adjust the concentration to be $1\times10^8$ CFU/mL, and the *Lycium barbarum* polysaccharide was added to adjust the concentration to be 20 mg/mL.

(2) Animal experiments: 70 SPF-grade Balb/c mice (purchased from Beijing Vital River Laboratory Animal Technology Co., Ltd.) aged 8 weeks were purchased and bred in the Center for Drug Safety Evaluation and Research, Nanjing University of Chinese Medicine, with code of ethics of 202304A075. The mice were given food normally, subjected to adaptive feeding for 1 week, and randomly grouped according to the body weight; oxaliplatin (purchased from MEDCHEMEXPRESS LLC., HY-17371, dissolved in 5% glucose solution) was intraperitoneally injected into the mice at 8 mg/kg/d for 5 days for modeling, and during modeling, the mice were intragastrically dosed at the same time, wherein the volume for intragastric administration was 0.1 mL/10 g/time/d per group, and the administration lasted for 10 days; the specific groups are shown in Table 2.

TABLE 2

| Group | Content of AKK bacteria | Content of polysaccharides |
|---|---|---|
| control | 0 | 0 |
| model | 0 | 0 |
| AKK | 1*$10^8$ CFU/mL | 0 |
| LBP-Z | 0 | 20 mg/mL |
| LBP-50-100 | 0 | 20 mg/mL |
| AL-Z | 1*$10^8$ CFU/mL | 20 mg/mL |
| AL-50-100 | 1*$10^8$ CFU/mL | 20 mg/mL |

2. Effects on Dietary Health of Mice

Figure 3:
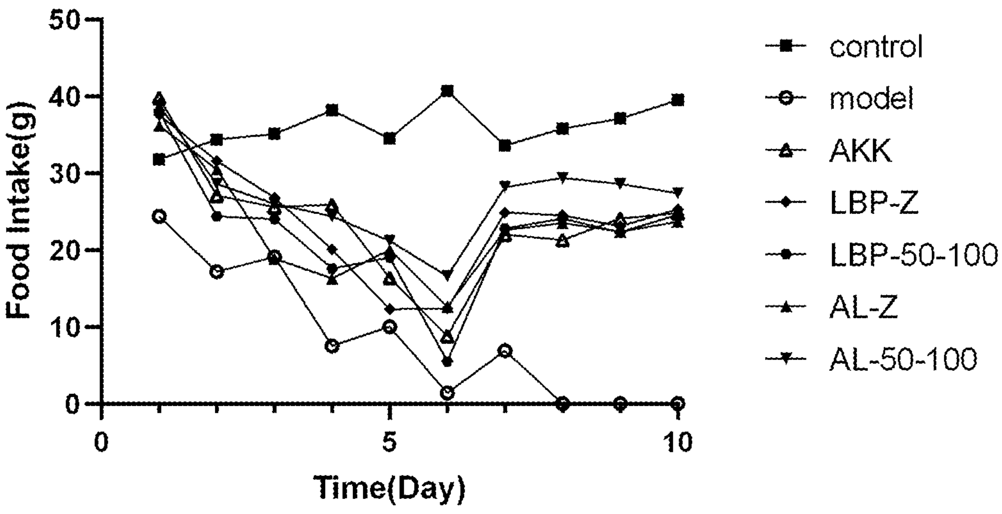
FIG. 3 shows the change in daily food intake of mice taking the formulation of the present invention after modeling.
Figure 4:
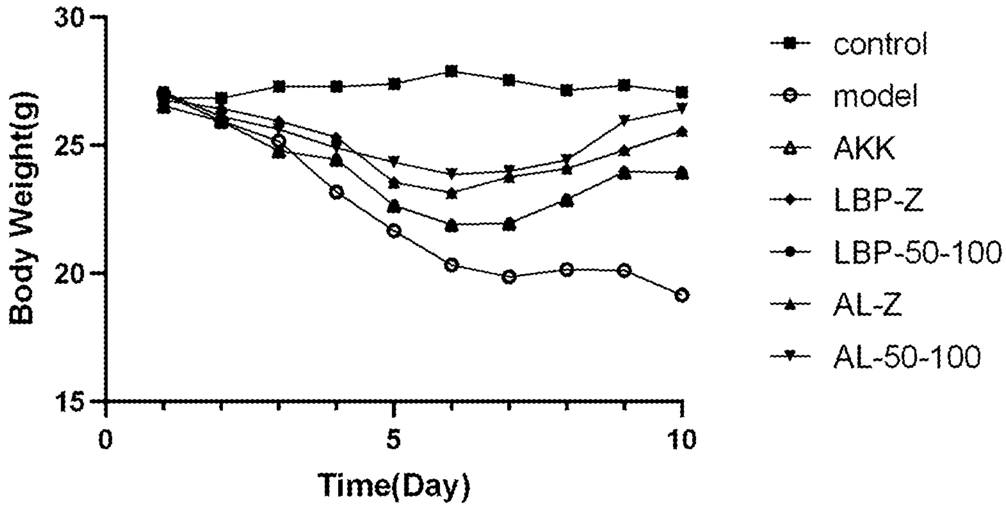
FIG. 4 shows the change in the body weight of mice taking the formulation of the present invention after modeling.

On the day before modeling, the feed weight and the body weight of the mice were weighed and recorded every day, and the daily food intake and the change of the body weight of the mice were calculated. The results are shown in FIGS. 3-4.

After the start of modeling, the average body weight of mice in each group injected with oxaliplatin significantly decreased as compared with the normal group, with the greatest decrease in the model group; compared with the model group, the effect was improved to a certain extent when the AKK or the *Lycium barbarum* polysaccharide was given alone, the effect was better when the AKK and the *Lycium barbarum* polysaccharide were given in combination, and the effect was optimal when the AKK and the LBP-50-100 were given in combination.

3. Effects on Immune Functions in Mice

After 12 h from the last administration, the mice were weighed, blood was collected from orbital veins, and the mice were sacrificed by cervical dislocation. Spleens were removed and weighed, the average spleen coefficients were calculated, and the results are shown in Table 3. The levels of cytokines TNF-α and IL-6 in serum were detected by using the Elisa kit, and the results are shown in FIGS. 5-6.

Figure 5:
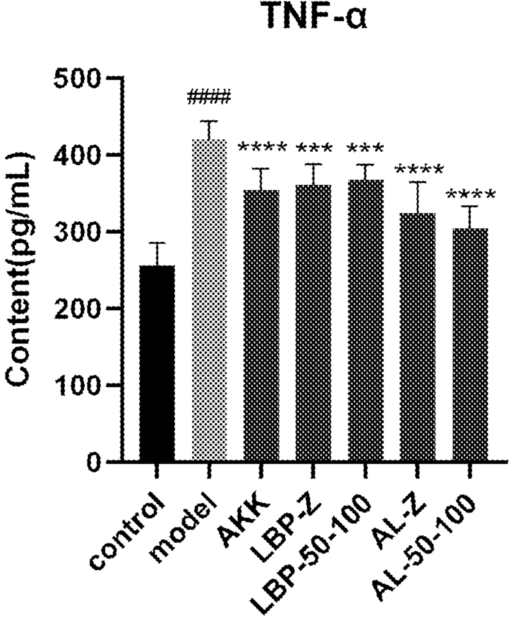
FIG. 5 shows the serum TNF-α levels in mice taking the formulation of the present invention after modeling.
Figure 6:
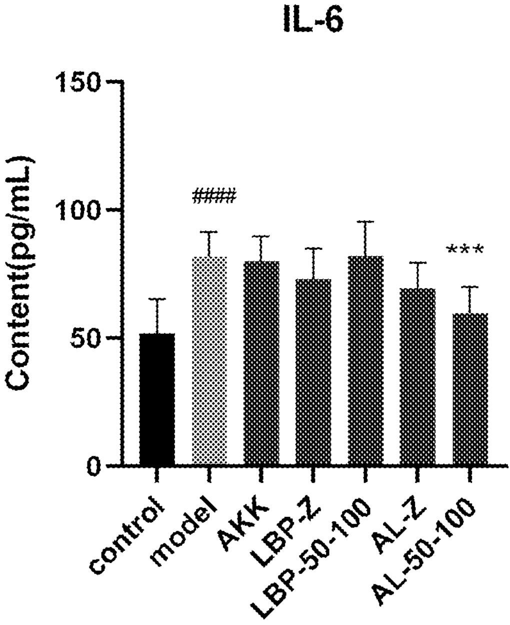
FIG. 6 shows the serum IL-6 levels in mice taking the formulation of the present invention after modeling.
Figure 7:
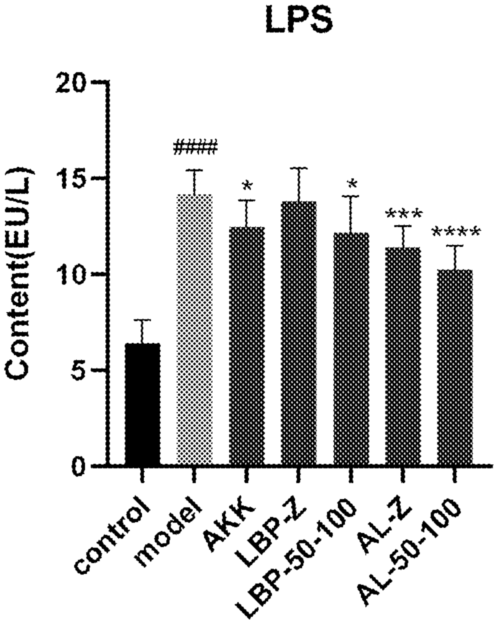
FIG. 7 shows the serum lipopolysaccharide (LPS) levels in mice taking the formulation of the present invention after modeling.

As can be seen from Table 3 and FIGS. 5-6, compared with the blank group, the spleen index of the model group after oxaliplatin injection significantly decreased, and the levels of TNF-α and IL-6 in serum significantly increased, indicating that the immune functions were impaired; compared with the model group, the spleen indexes of the administration groups all increased, and the TNF-α and IL-6 levels were obviously lower than those of the model group.

TABLE 3

| Group | Spleen index |
|---|---|
| control | 0.352 |
| model | 0.172 |
| AKK | 0.205 |
| LBP-Z | 0.216 |
| LBP-50-100 | 0.219 |
| AL-Z | 0.219 |
| ALZ-50-100 | 0.234 |

4. Effects on Intestinal Barrier in Mice

Figure 8:
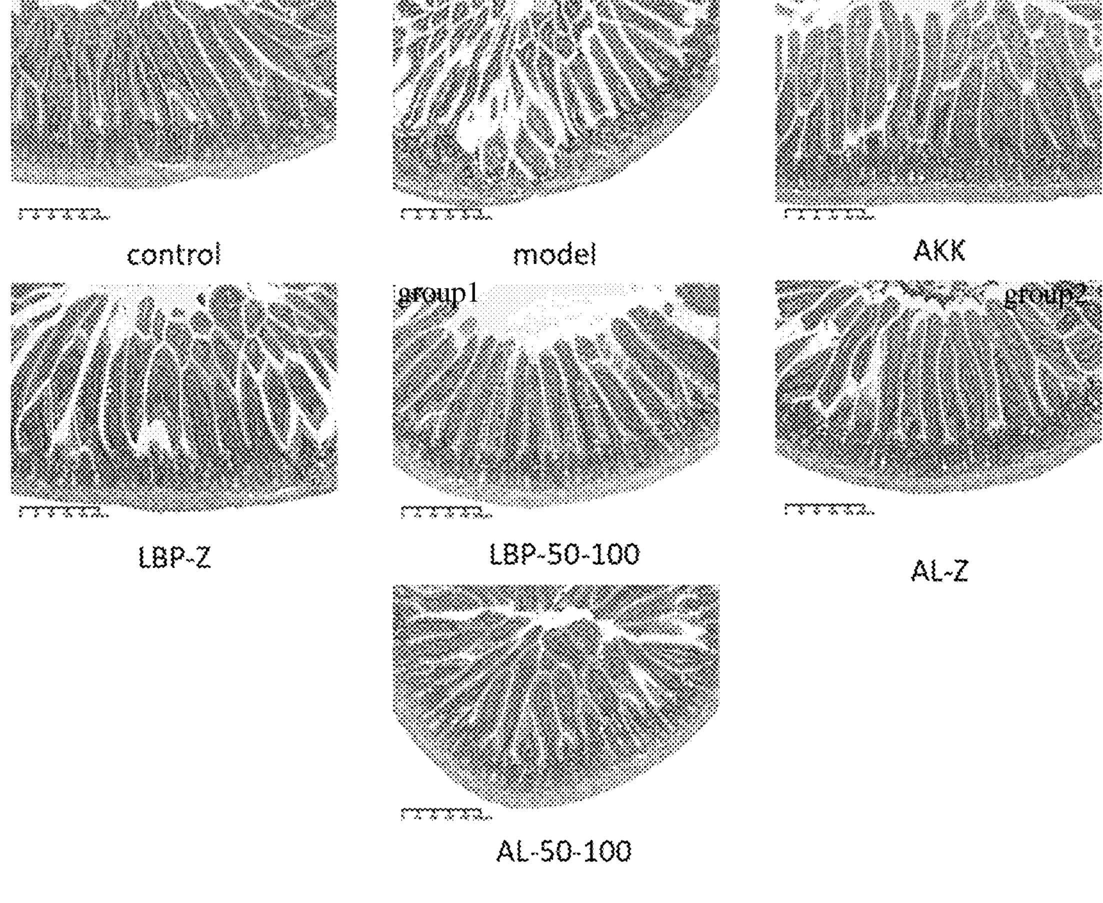
FIG. 8 shows sections of the small intestine of mice taking the formulation of the present invention after modeling.

The serum lipopolysaccharide (LPS) levels of the mice were detected by using the Elisa kit, and the results are shown in FIG. 8. After the mice were sacrificed by cervical dislocation, 1 cm of jejunum close to the segment of duodenum was taken, the content was washed with normal saline, the jejunum was fixed with 4% paraformaldehyde solution, and then trimmed, dehydrated, embedded, sliced and stained, and the shape of the sections of the small intestine was observed under an optical microscope.

As shown in FIG. 8, compared with the blank group, the mice injected with oxaliplatin in the model group had serious intestinal villus loss, impaired intestinal barrier, and increased permeability, resulting in increased serum LPS. The structure and villi of the intestinal mucosa of the mice in the blank group were complete and clear in outline, the arrangement was compact and tidy, and the villus epithelial cells were continuous and complete. The mice in the model group had obvious intestinal mucosa injury and obvious shedding of villus epithelial cells, and meanwhile, it was found that intestinal villi were damaged and obviously shortened and crypts became shallow. Compared with the model group, LPS levels and intestinal sections of other groups were significantly improved, and the effect was optimal when AKK and LBP-50-100 were given in combination.

In conclusion, it is suggested that the *Lycium barbarum* polysaccharides and the AKK can enhance the intestinal immunity to a certain extent, relieve the injury caused by oxaliplatin and protect intestinal barriers, and have a synergistic effect when being given together. The combined formulation of the *Lycium barbarum* polysaccharide and the *Akkermansia muciniphila* of the present invention can be used as an adjuvant drug of oxaliplatin for ameliorating adverse effects thereof.

What is claimed is:

1. A combined formulation capable of ameliorating gastrointestinal adverse effects caused by oxaliplatin in mammals, comprising a purified *Lycium barbarum* polysaccharide with a molecular weight of $9.19\times10^4$ Da and *Akkermansia muciniphila* ATCC BAA-835; wherein gastrointestinal adverse effect is selected from the group consisting of diarrhea, nausea, vomiting, mucositis, loss of appetite, and intestinal barrier impairment.

2. The combined formulation according to claim 1, wherein the formulation is in the form of a capsule, and the capsule further comprises an edible excipient, wherein the excipient comprises one or more of a diluent, a lyoprotectant, a suspending agent, a flavoring agent, and a solubilizer.

3. The combined formulation according to claim 1, wherein the *Lycium barbarum* polysaccharide is prepared by the following method:

(1) taking *Fructus lycii*, adding 80% ethanol at a volume ratio of 1:8-1:20, and continuously performing reflux extraction for 1-3 h to obtain an ethanol extract and residues;

(2) adding water into the residues obtained in the step (1) at a ratio of 1:8-1:10, and continuously performing reflux extraction for 1-3 h to obtain a water extract;

(3) concentrating the water extract obtained in the step (2), lyophilizing a part of the concentrated solution to obtain an unpurified *Lycium barbarum* polysaccharide, and purifying a part of the concentrated solution by using a hollow fiber ultrafiltration device to obtain a retention solution; and (4) precipitating the retention solution obtained in the step (3) in ethanol, collecting a precipitate, and lyophilizing the precipitate to obtain *Lycium barbarum* polysaccharides with different molecular weights.

4. The combined formulation according to claim 3, wherein the *Lycium barbarum* polysaccharide is prepared by the following method:

(1) taking *Fructus lycii*, adding 80% ethanol at a volume ratio of 1:10, and continuously performing reflux extraction for 2 times (2 h each time) to obtain an ethanol extract and residues;

(2) adding water into the residues obtained in the step (1) at a ratio of 1:10, and continuously performing reflux extraction for 2 times (2 h each time) to obtain a water extract;

(3) concentrating the water extract obtained in the step (2), lyophilizing a part of the concentrated solution to obtain an unpurified *Lycium barbarum* polysaccharide, and purifying a part of the concentrated solution by using a hollow fiber ultrafiltration device to obtain a retention solution, wherein ultrafiltration membrane retention capacities are 100 KDa, 50 KDa and 3 KDAa in sequence, and ultrafiltration conditions are 0.1 MPa, 27° C. and 1 g/L; and (4) adding ethanol into the retention solution obtained in the step (3) until a content of the ethanol is 75%, standing for 24 h, collecting a precipitate, and lyophilizing the precipitate to obtain *Lycium barbarum* polysaccharides with different molecular weights.

5. The combined formulation according to claim 1, wherein a bacterial powder of the *Akkermansia muciniphila* is prepared by the following method:

(1) taking out a cryopreserved strain, thawing the cryopreserved strain in a liquid culture medium, and performing subculturing to obtain a bacterial solution;

(2) centrifuging the bacterial solution obtained in the step (1), collecting a precipitate, and washing the precipitate with normal saline to obtain a bacterial sludge; and (3) adding a composite lyoprotectant into the bacterial sludge obtained in the step (2), and lyophilizing the mixture to obtain the bacterial powder.

6. The combined formulation according to claim 5, wherein the liquid culture medium used in the step (1) is BHI brain-heart leach liquor+0.25% mucin, and an inoculation amount is 5% per passage;

centrifugation conditions of the step (2) are 7500 r/min, 4° C. and 15 min;

a volume ratio of an addition amount of the composite lyoprotectant to the bacterial sludge in the step (3) is 1:1; the composite lyoprotectant is a solution of 12% by mass of sweet whey powder, 0.4% by mass of glycine, 1.2% by mass of mannitol and 0.2% by mass of VC sodium in percentage by mass prepared from normal saline.

7. A method for treating and ameliorating the gastrointestinal adverse effect caused by the oxaliplatin in mammals comprising a step of administering a subject in need with the combined formulation of claim 1.

* * * * *